United States Patent [19]

Luber et al.

[11] Patent Number: 6,103,260
[45] Date of Patent: *Aug. 15, 2000

[54] SIMETHICONE/ANHYDROUS CALCIUM PHOSPHATE COMPOSITIONS

[75] Inventors: Joseph R. Luber, Quakertown; Glenn Madison, Lansdale; Gerard McNally, Strafford, all of Pa.

[73] Assignee: McNeil-PPC, Inc., Skillman, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/896,189

[22] Filed: Jul. 17, 1997

[51] Int. Cl.[7] ............... A61K 9/16; A61K 9/20; A61K 9/48; A61K 9/50
[52] U.S. Cl. ............ 424/452; 424/435; 424/441; 424/451; 424/456; 424/464; 424/465; 424/489; 424/490; 514/770; 514/781; 514/951
[58] Field of Search ................... 424/441, 451, 424/456, 464, 465, 489, 452, 435, 490

[56] References Cited

U.S. PATENT DOCUMENTS

| | | | |
|---|---|---|---|
| 4,127,650 | 11/1978 | Buehler | 424/184 |
| 4,396,604 | 8/1983 | Mitra | 424/154 |
| 4,557,916 | 12/1985 | Withiam | 423/328 |
| 4,906,478 | 3/1990 | Valentine et al. | 424/682 |
| 5,073,384 | 12/1991 | Valentine et al. | 424/474 |
| 5,275,822 | 1/1994 | Valentine et al. | 424/489 |
| 5,458,886 | 10/1995 | Briquet | 424/451 |
| 5,599,577 | 2/1997 | Stevens et al. | 427/2.14 |

FOREIGN PATENT DOCUMENTS

| | | |
|---|---|---|
| 263224 | 4/1988 | European Pat. Off. . |
| 465234 | 1/1992 | European Pat. Off. . |
| 571217 | 11/1993 | European Pat. Off. . |
| 914925 | 1/1960 | United Kingdom . |

OTHER PUBLICATIONS

European Search Report Application No. 98305696 dated Oct. 22, 1998.

*Primary Examiner*—Thurman K. Page
*Assistant Examiner*—James M. Spear

[57] ABSTRACT

The invention relates to antifoam oral solid dosage form preparations formed from a free flowing granular composition comprising an admixture of simethicone and either one or both of granular anhydrous tribasic calcium phosphate or dibasic calcium phosphate wherein the admixture is a uniform granular composition of not more than 1000 micron particle size which is suitable for compression into a solid dosage form for oral administration.

12 Claims, No Drawings

SIMETHICONE/ANHYDROUS CALCIUM PHOSPHATE COMPOSITIONS

BACKGROUND OF THE INVENTION

1. Field of the Invention

The present invention relates to antigas/antiflatulent oral solid pharmaceutical dosage forms comprising an admixture of simethicone and anhydrous tribasic or dibasic calcium phosphate, free flowing granular compositions for preparing such dosage forms and methods for their production.

2. Background

Simethicone is a mixture of fully methylated linear siloxane polymers containing repeating units of polydimethylsiloxane stabilized with trimethylsiloxy end-blocking units, and silicon dioxide. Simethicone contains 90.5–99% of polydimethylsiloxane and 4–7% silicon dioxide. The polydimethylsiloxanes present in simethicone are practically inert polymers having a molecular weight of 14,000–21,000. The mixture is a gray, translucent, viscous fluid which is insoluble in water.

When administered orally, simethicone is used as an adjunct in the symptomatic treatment of flatulence, functional gastric bloating, and postoperative gas pains. The clinical use of simethicone is based on its antifoam properties. Silicone antifoams spread on the surface of aqueous liquids, forming a film of low surface tension and thus causing the collapse of foam bubbles. Thus for self medication in over-the-counter preparations, simethicone is used as an antiflatulent to relieve symptoms commonly referred to as gas, including upper GI bloating, pressure, fullness, or stuffed feeling. It is often combined with other gastrointestinal medications, such as antacids, antispasmodics or digestive enzymes and various simethicone formulations are disclosed in the prior art.

Simethicone can be administered orally as a liquid preparation or as solid form for example capsules, chewable or swallowable tablets. The preferred form for ease of administration is a swallowable tablet. The advantage of tablets over liquids is the ease of portability. The advantages of swallowable tablets over chewable tablets include the ease of ingestion and lack of taste. Film coated or gelatin coated tablets are preferred for swallowable tablets.

Historically, in preparing solid simethicone dosage forms, difficulties have been encountered when attempting to incorporate substantial quantities of the liquid simethicone in the solid final blend for tableting. The difficulty has been to achieve sufficient cohesion in the compact for compression, particularly for direct compression tableting, so that the tablet will withstand the rigors of further processing, i.e. film coating, gelatin dipping, printing, packaging and the like. Likewise, difficulties have been encountered in assuring that the viscous liquid simethicone is uniformly distributed throughout the solid formulation and expeditiously dispersed upon administration.

An object of the present invention, therefore, is to provide a composition and process wherein substantial quantities of liquid simethicone can be incorporated into solid tablet formulations for manufacture by a dry blend/direct compression process.

U.S. Pat. No. 4,906,478 discloses a simethicone preparation comprising a powdered combinate of particulate calcium silicate and simethicone. U.S. Pat. No. 5,073,384 discloses simethicone preparations comprising combinates of water soluble agglomerated maltodextrin and simethicone. U.S. Pat. No. 5,458,886 discloses a free-flowing granular composition comprising titanium dioxide having specific particle size and surface area in combination with simethicone. While these methods are of some benefit in achieving a simethicone composition suitable for the dry blend/direct compression manufacturing process, the present invention provides further improvements to accomplish the object of providing a composition which may be easily and inexpensively formulated into potent swallowable or chewable tablets.

SUMMARY OF THE INVENTION

The invention relates to antifoam oral solid dosage form preparations formed from a free flowing granular composition comprising an admixture of simethicone and either one or both of granular anhydrous tribasic calcium phosphate or dibasic calcium phosphate wherein the admixture is a uniform granular composition of not more than 1000 micron particle size which is suitable for compression into a solid dosage form for oral administration. The granular anhydrous tribasic or dibasic calcium phosphate comprises about 30–90% w/w of the admixture combinate. The simethicone comprises about 10–70% w/w of the admixture combinate. In a preferred embodiment, the combinate further comprises 0.5 to 4% w/w of a silicone dioxide or 1.0–30.0% w/w of anhydrous calcium phosphate powder. The free flowing granular composition is admixed with conventional tablet binders and excipients and is compressed into the solid oral dosage forms. Preferably, the simethicone comprises greater than about 8% and less than about 20% w/w of the final blend for compression.

In another aspect of the invention, a process for producing a free flowing granular composition of a simethicone antifoam agent for compression into solid oral dosage forms is provided which comprises forming an admixture of granular anhydrous tribasic or dibasic calcium phosphate, the simethicone antifoam agent and optionally a silicon dioxide or anhydrous calcium phosphate powder by adding the simethicone to the granular tribasic or dibasic calcium phosphate and the optional silicon dioxide or anhydrous calcium phosphate powder, dry blending until uniform and shearing to assure a uniform powder. In a further aspect of the process, the granular composition is then combined with excipient materials or other active ingredients and compressed to provide the solid oral dosage form, preferably in the form of a compressed tablet, which may be further processed by coating with an aqueous film coating or enteric coating and/or gelatin dipped and printed.

Benefits of the anhydrous calcium phosphates/simethicone combinate of the present invention over the aforementioned prior art compositions are that it is both a more free flowing and more stable admixture than one comprising agglomerated maltodextrin/simethicone and it is not prone to separation of the simethicone from the substrate. A benefit over the composition of U.S. Pat. No. 4,906,478 is that the anhydrous calcium phosphate/simethicone combinates have significantly better defoaming activity as measured by U.S. Pharmacopia standards (USP 23, page 1411(Simethicone Tablets monograph).

DETAILED DESCRIPTION

As indicated, the dosage forms of the present invention contain an antifoam agent such as simethicone as an active ingredient. The simethicone preferably conforms to the United States Pharmacopoeia (USP XXII) definition, that is, a mixture of fully methylated linear siloxane polymers containing repeating units of the formula $(\text{---}(CH_3)_2SiO\text{---})_n$, stabilized with trimethyl siloxy end-blocking units of the formula (—(CH$_3$)$_3$—SiO—) and silicon dioxide. Other organopolysiloxane antifoam agents are known in the art and may also be used as the active ingredient in this invention. Such organopolylosiloxane antifoam agents are disclosed, for example, in U.S. Pat. No. 5,458,886, and the references discussed therein, hereby incorporated by reference. Typically, the antifoam agents are viscous liquid or paste-like materials. At standard temperature and pressure, simethicone is described as a water-white to gray, translucent, viscous oil-like liquid with a density of 0.965–0.970 grams per cubic centimeter and is immiscible with water and alcohol. Thus, the present invention provides a method for forming free flowing granular compositions from such viscous oily liquid or paste-like antifoam agents, which granular compositions are suitable for compression into solid oral dosage forms.

The amount of simethicone or other organopolysiloxane antifoam agent contained in the solid oral dosage form should be sufficient to provide a therapeutic dosage to a patient suffering from gas or flatulence and associated symptoms. The preferred dosage range for simethicone is in the range of about 20 mg to about 125 mg per dosage unit, generally not to exceed 500 mg/day. The dosage ranges may vary for age and weight of a patient as well as the severity of symptoms.

The tribasic or dibasic calcium phosphate is essentially in the anhydrous form. Commercial forms of anhydrous tribasic or dibasic calcium phosphates are available from Rhone-Poulenc; Mendell and FMC Corp.

In accordance with the present invention, the simethicone is admixed with the granulated anhydrous tribasic or dibasic calcium phosphate to form a uniform free flowing granular composition. Generally, it is desired that the admixture contain a proportionate amount of the simethicone antifoam agent and granular anhydrous calcium phosphate which is consistent with forming a free-flowing granular composition. Preferably, the proportionate amounts of the ingredients of the granular admixture composition is about 10–70% w/w simethicone and about 30–90% w/w granular anhydrous tribasic or dibasic calcium phosphate. The ingredients are blended, sheared and screened to assure a free flowing granular composition of not more than about 1000 micron particle size. Optionally, the granular composition may also contain an amount of a silicone dioxide or anhydrous calcium phosphate powder, preferably Silicon Dioxide NF in an amount of about 0.5–4% w/w or anhydrous calcium phosphate powder in an amount of about 1.0–30.0% w/w of the granular composition.

The simethicone/granular anhydrous calcium phosphate admixture composition is conveniently prepared by a dry blend procedure. The anhydrous tribasic or dibasic calcium phosphate is first granulated either by dry compaction or by wet granulation/drying, preferably by dry compaction. Next, the simethicone compound is added to a moving bed of granular anhydrous tribasic or dibasic calcium phosphate so that the simethicone is uniformly distributed and the granular anhydrous calcium phosphate particle size remains essentially unchanged. The bed is kept in motion by low shear mixers. After the granular anhydrous tribasic or dibasic calcium phosphate bed has absorbed the simethicone and a finely divided granular composition is maintained, the silicon dioxide or anhydrous calcium phosphate powder may be added. The granulation may then be screened through a No. 20 US Standard screen (about 840 microns).

The solid oral dosage forms of the present invention may be prepared in the form of tablets, caplets, gelcaps, capsules, chewable tablets, lozenges, fast dissolving wafers, and other known and effective delivery modes. The free flowing granular simethicone/anhydrous tribasic or dibasic calcium phosphate composition may be admixed with a variety of pharmaceutically acceptable excipients including fillers, binders, sweeteners, artificial sweeteners, lubricants, glidants, disintegrants, colors, adsorbents, acidifying agents, and flavoring agents. The choice of excipient will depend on the solid oral dosage form employed (i.e. tablets, caplets, or capsules) and whether the dosage form is chewable or a swallowable formulation. Swallowable oral tablets prepared by direct compression are preferred. Excipients which are compatible with direct compression tablet formulations are preferred. For example, excipients chosen from the following list may be employed:

a) diluents such as lactose, kaolin, mannitol, crystalline sorbitol, additional dibasic or calcium phosphates and the like;

b) binders such as sugars, microcrystalline cellulose, carboxymethyl cellulose, hydroxyethyl cellulose, polyvinylpyrrolidone and the like;

c) lubricants such as magnesium stearate, talc, calcium stearate, zinc stearate, stearic acid, hydrogenated vegetable oil, leucine, glycerides and sodium stearyl fumarate;

d) disintegrants such as starches, croscarmellose sodium, methylcellulose, agar, bentonite, alginic acid, carboxymethylcellulose, polyvinylpyrrolidone and the like;

e) scavengers such as charcoal, silicon dioxide, anhydrous calcium phosphates;

f) flavoring agents such as mannitol, dextrose, fructose, sorbitol and the like; and g) coloring agents.

Other suitable excipients can be found in the *Handbook of Pharmaceutical Excipients*, published by the American Pharmaceutical Association, herein incorporated by reference.

A typical dosage form of the present invention may have a formulation containing various components in accordance with the following:

| Free flowing Simethicone Admixture | 10% to 99% |
| --- | --- |
| Tribasic Calcium Phosphate, Anhydrous | 45% to 80% |
| Simethicone USP | 10% to 50% |
| Scavenger e.g. Silicon Dioxide, NF or Anhydrous Calcium Phosphate Powder | 1% to 10% |
| Excipients | 1% to 90% |
| Diluent | 0% to 40% |
| Binders | 0% to 10% |
| Lubricant | 0% to 1.5% |
| Scavenger | 0% to 10% |
| Flavorant/Colorants | 0% to 5% |

Preferably, the simethicone content of the final tablet formulation comprises about 8% to about 20% w/w of the final blend. The production of the oral dosage forms of the invention are carried out by methods known in the art, for example, by granulating the anhydrous tribasic or dibasic calcium phosphate using either dry compaction or wet granulation techniques; forming the free flowing simethicone/granular anhydrous tribasic or dibasic calcium phosphate admixture; mixing the free flowing simethicone/granular anhydrous tribasic or dibasic calcium phosphate composition with the excipients and then forming the composition into the dosage form by methods known in the art, for example by direct compression, dry granulation or the like. Suitable manufacturing methods for oral solid dosage forms are disclosed in *Remington's Pharmaceutical Science,* 18th Edition, published by Mack Publishing Company, hereby incorporated by reference. Preferably, the manufacturing procedure generally involves preparing the free flowing simethicone/granular anhydrous tribasic or dibasic calcium phosphate admixture as described above, adding the additional binder/diluent/disintegrant excipients with low shear blending, adding a lubricant and preparing tablets by direct compression.

Optionally, the dosage form can include one or more additional active ingredients suitable for the treatment of gastrointestinal disorders, for example heartburn, ulcers or diarrhea. Suitable active agents for treating gastrointestinal disorders include heartburn or antiulcer medicaments such as sucralfate, the H2 receptor antagonists cimetidine, ranitidine, famotidine or nizatidine, proton pump inhibitors such as omeprazole or lansoprazole; antidiarrheal agents such as loperamide and diphenoxylate; gastrointestinal motility agents such as cisapride, and antacids such as aluminum hydroxide, magnesium carbonate, magnesium hydroxide, calcium carbonate and the like. The amount of such additional active ingredient combined with the simethicone should be an amount sufficient to provide a therapeutic dosage to a patient suffering from the gastrointestinal disorder being treated.

The following examples are provided to further illustrate the present invention:

EXAMPLE 1

Preparation of Simethicone/Granular Anhydrous Tribasic Calcium Phosphate Admixture 1. 700 gm of granular tricalcium phosphate (Tritab®, Rhone-Poulenc, Shelton, Conn.) is added to the mixing bowl of a Kitchen Aid mixer.
2. While mixing at low speed, over a period of 5 minutes add 200 gm of simethicone, USP.
3. Continue mixing at low speed for an additional 5 minutes.
4. Add 2.5 gm of silicon dioxide and mix an additional 5 minutes.

This intermediate is a free flowing granulation with no large agglomerates.

EXAMPLE 2

Preparation of Simethicone/Granular Anhydrous Dibasic Calcium Phosphate Admixture 1) 700 gm of granular anhydrous dibasic calcium phosphate, (Emcompress® Anhydrous, Mendell, Paterson, N.J.) is added to the mixing bowl of a Kitchen Aid mixer.
2) While mixing a low speed, over a period of 5 minutes add 200 gm of simethicone, USP.
3) Continue mixing at low speed for an additional 5 minutes.
4) Add 7.5 gm of silicon dioxide and mix an additional 5 minutes.

This intermediate is a free flowing granulation with no large agglomerates.

COMPARATIVE EXAMPLE 2

Preparation of Simethicone/Granular Dibasic Calcium Phosphate Dihydrate Admixture 1) 700 gm of granular Dicalcium phosphate, Dihydrate (Emcompress®, Mendell, Paterson, N.J.) is added to the mixing bowl of a Kitchen Aid mixer.
2) While mixing at low speed, over a period of 5 minutes add 200 gm of simethicone, USP.
3) Continue mixing at low speed for an additional 5 minutes.
4) Add 30 gm of silicon dioxide and mix an additional 5 minutes.

This intermediate is NOT a free flowing granulation. It contains many large agglomerates.

EXAMPLE 3

Preparation of Chewable Tablets Containing Simethicone/Granular Anhydrous Tribasic Calcium Phosphate Admixture 1) 89 gm of the free flowing granular intermediate from Example 1 was then blended with 98 gm of Dextrates, 7.5 gm granular sorbitol, 0.6 gm peppermint flavor, and 0.5 gm stearic acid.
2) The blend was finally compressed using ⅝" FFBE tooling. The tablet weight was 1300 mg. The physical properties of the tablet were:

Hardness: 8–10 kp

Friability: less than 0.1% at 100 drops

Disintegration in water: less than 1 minute

Defoam: 5 secs.

EXAMPLE 4

Preparation of Chewable Tablets Containing Simethicone/Granular Anhydrous Tribasic Calcium Phosphate Admixture 1) 1500 gm of tricalcium phosphate powder was dry granulated by roller compacting at a roll pressure of 500 psi.
2) The compact was passed through a Fitz Mill with a 0.093" screen, knives forward.
3) The milled material was screened, and the -30 to +80 mesh fraction collected as product.
4) 700 gm of compacted tricalcium phosphate granules was added to the mixing bowl of a Kitchen Aid mixer.
5) While mixing a low speed, over a period of 5 minutes add 200 gm of simethicone, USP.
6) Continue mixing at low speed for an additional 5 minutes.
7) Add 20 gm of tricalcium phosphate powder and mix an additional 5 minutes.

This intermediate is a free flowing granulation with no large agglomerates.

8) 91 gm of the above intermediate was then blended with 98 gm of Dextrates, 7.5 gm granular sorbitol, 0.6 gm peppermint flavor, and 0.5 gm stearic acid.
9) The blend was finally compressed using ⅝" FFBE tooling. The tablet weight was 1300 mg. The physical properties of the tablet were:

Hardness: 11–12 kp

Friability: less than 0.1% at 100 drops

Disintegration in N/10 HCl: less than 1.5 minute

Defoam: 7 secs

EXAMPLE 5

Preparation of Chewable Tablets Containing Simethicone/Granular Anhydrous Tribasic Calcium Phosphate Admixture 1) 500 gm of tricalcium phosphate powder and 50 gm of pregel starch were dry blended in a Kitchen Aid mixer.

2) 310 gm of purified water was slowly added to the mixer with continuous mixing.
3) The wet granulation was passed through a #12 mesh screen and then dried for 5 hours at 50° C.
4) The dried granules were passed through a #18 mesh screen and material less than #70 mesh was removed.
5) Steps 1–4 were repeated.
6) Then 700 gm of granulated tricalcium phosphate/pregel starch granules is added to the mixing bowl of a Kitchen Aid mixer.
7) While mixing a low speed, over a period of 5 minutes add 200 gm of simethicone, USP.
8) Continue mixing at low speed for an additional 5 minutes. This intermediate is a free flowing granulation with no large agglomerates.
9) 89 gm of the above intermediate was then blended with 98 gm of Dextrates, 7.5 gm granular sorbitol, 0.6 gm peppermint flavor, and 0.5 gm stearic acid.
10) The blend was finally compressed using 5/8" FFBE tooling. The tablet weight was 1300 mg, and its physical properties were:

Hardness: 8–9 kp
Friability: less than 0.1% at 100 drops
Disintegration in N/10 HCl: less than 1 minute
Defoam: 5 secs.

EXAMPLE 6

Preparation of Swallowable Film Coated Tablets Containing Simethicone/Granular Anhydrous Tribasic Calcium Phosphate Admixture

| Ingredient | Qty mg/tab |
|---|---|
| PART I - concentrate | |
| Tribasic calcium phosphate, NF, Anhydrous, granular | 500 |
| Simethicone, USP | 125 |
| Tribasic calcium phosphate, NF, Anhydrous, Powder | 25 |
| PART II- Scavenger | |
| Tribasic calcium phosphate, NF, Anhydrous, Powder | 20 |
| PART III- Excipient/Binder system | |
| Dibasic calcium phosphate, Dihydrate, USP | 105.75 |
| Microcrystalline cellulose, NF (MCC) | 53 |
| Crystalline sorbitol, NF | 70 |
| Croscarmellose sodium, NF | 30 |
| PART IV-Lubricant | |
| Magnesium Stearate, NF | 0.5 |

PART 1) A concentrate comprised of granular and powdered anhydrous tribasic calcium phosphates, and simethicone is prepared by adding simethicone compound, USP to a moving bed of granular tribasic calcium phosphate so that the simethicone is distributed evenly and the granular calcium phosphate particle size remains essentially unchanged. The bed is kept in motion by low shear mixers such as fluid bed, Nauta, PK without intensifier bar, pin mixer, or ribbon mixer. After the bed has adsorbed the simethicone, anhydrous tribasic calcium phosphate powder is added. The granulation may then be screened through a No. 20 US Std screen (~840 micron).
PART 2) When a final blend for compression is desired an additional quantity of calcium phosphate powder is added to the PART 1 concentrate and blended.
PART 3) Excipients including a disintegrant are then added with low shear blending which imparts uniform distribution of the active within a binding matrix of limited compositional range.
PART 4) The final addition step is to add a lubricant.
PART 5) The blend is compressed into tablets using a rotary tablet press.
PART 6) Tablets are then film coated and/for gelatin dipped.

Typical film coated tablet characteristics:
Hardness range: 6–14 kp
Tablet weight (core): Approx. 1000 mg
USP disintegration time in water : Less than 7 minutes, in acid media : Less than 6 minutes
USP Defoaming activity time: 9 seconds

We claim:

1. An antifoam simethicone free-flowing granular composition suitable for use as an oral solid dosage form preparation formed by (i) preparing a granular composition consisting essentially of an admixture of (a) simethicone and (b) granular anhydrous tribasic or dibasic calcium phosphate or a mixture thereof; wherein the simethicone is adsorbed by the granular anhydrous tribasic or dibasic calcium phosphate or mixture thereof, and wherein the simethicone/calcium phosphate admixture is a uniform granular composition of not more than 1000 micron particle size, and (ii) admixing the uniform granular composition with one or more excipients to form the free-flowing granular composition.

2. An oral solid dosage form of claim 1 wherein said dosage form is in the form of a unit dose compressed swallowable or chewable tablet, or caplet, gelcap, capsule, lozenge or fast dissolving wafer.

3. An oral solid dosage form of claim 1 further containing one or more excipients in addition to said free flowing granular composition.

4. An oral solid dosage form of claim 3 wherein said excipients are selected from one or more fillers, binders, sweeteners, artificial sweeteners, lubricants, glidants, disintegrants, colors, adsorbents, acidifying agents, and flavoring agents.

5. An oral solid dosage form of claim 1 wherein the simethicone content of the dosage form comprises about 8% to about 20% w/w.

6. An oral solid dosage form of claim 5 further containing crystalline sorbitol, microcrystalline cellulose and anhydrous tribasic or dibasic calcium phosphate as excipients in addition to the free flowing granular composition of simethicone and granular anhydrous tribasic or dibasic calcium phosphate.

7. An antifoam simethicone oral solid dosage form preparation formed by (i) preparing a free-flowing granular composition consisting essentially of an admixture of (a) simethicone and (b) granular anhydrous tribasic or dibasic calcium phosphate or a mixture thereof; wherein the simethicone is adsorbed by the granular anhydrous tribasic or dibasic calcium phosphate or mixture thereof to form the free-flowing granular composition, and wherein the simethicone/calcium phosphate admixture is a uniform granular composition of not more than 1000 micron particle size, and (ii) admixing the free-flowing granular composition with one or more excipients and one or more additional active ingredients suitable for the treatment of gastrointestinal disorders, to form the oral solid dosage form preparation.

8. The oral solid dosage form of claim 7 wherein the additional active ingredient is selected from one or more of the following: H2 receptor antagonists, proton pump inhibitors, antidiarrheal agents, gastrointestinal motility agents, and antacids.

9. A free flowing granular composition comprising an admixture of (a) simethicone and (b) granular anhydrous tribasic or dibasic calcium phosphate or a mixture thereof; wherein the simethicone/calcium phosphate admixture is a uniform granular composition of not more than 1000 micron particle size.

10. The free flowing granular composition of claim 9 wherein the proportionate amounts of the ingredients of the granular admixture composition is about 10–70% w/w simethicone and about 30–90% w/w granular anhydrous tribasic or dibasic calcium phosphate.

11. The free flowing granular composition of claim 9 further containing either Silicon Dioxide in an amount of about 0.5–4% w/w or anhydrous calcium phosphate powder in an amount of about 1–30% w/w of the granular composition.

12. A process for producing a free flowing granular composition of a simethicone antifoam agent for compression into solid oral dosage forms which comprises forming an admixture of granular anhydrous tribasic and/or dibasic calcium phosphate, the simethicone antifoam agent and optionally a scavenger by adding the simethicone to the granular anhydrous tribasic or dibasic calcium phosphate and the optional scavenger, dry blending until uniform and shearing to assure a uniform free flowing granular composition.

* * * * *